United States Patent
Moinet et al.

(10) Patent No.: US 8,217,040 B2
(45) Date of Patent: Jul. 10, 2012

(54) USE OF TRIAZINE DERIVATIVES FOR THE MANUFACTURE OF A MEDICAMENT HAVING A CICATRISING OR ANGIOGENIC EFFECT

(75) Inventors: Gérard Moinet, Orsay (FR); Daniel Cravo, Montesson (FR)

(73) Assignee: Poxel SAS, Lyon (FR)

( * ) Notice: Subject to any disclaimer, the term of this patent is extended or adjusted under 35 U.S.C. 154(b) by 277 days.

(21) Appl. No.: 12/160,515

(22) PCT Filed: Dec. 18, 2006

(86) PCT No.: PCT/EP2006/012183
§ 371 (c)(1),
(2), (4) Date: Jul. 10, 2008

(87) PCT Pub. No.: WO2007/079915
PCT Pub. Date: Jul. 19, 2007

(65) Prior Publication Data
US 2010/0168115 A1    Jul. 1, 2010

(30) Foreign Application Priority Data
Jan. 13, 2006 (FR) .................................. 06 00347

(51) Int. Cl.
*A01N 43/66* (2006.01)
*A61K 31/53* (2006.01)

(52) U.S. Cl. ....................................................... 514/245
(58) Field of Classification Search ................... 514/245
See application file for complete search history.

(56) References Cited

U.S. PATENT DOCUMENTS

| 6,150,362 A * | 11/2000 | Henkin et al. ................. 514/245 |
| 7,622,469 B2 * | 11/2009 | Maeda et al. .................. 514/245 |
| 2003/0109530 A1 * | 6/2003 | Moinet et al. .................. 514/245 |

FOREIGN PATENT DOCUMENTS

| WO | WO 99/31088 A | 6/1999 |
| WO | WO 01/55122 A | 8/2001 |
| WO | WO 2004/089917 A | 10/2004 |

OTHER PUBLICATIONS

Cooper, A review of the evidence for the use of topical antimicrobial agents in wound care (2004) 1-15.*
Alikhani et al. (J. Biol. Chemistry 2005; 250(130 12087-12095).*
Martin et al. (Medical Research Reviews 23(2), 117-145, (2003).*
Aminian et al (www.ams.ac.ir (2003, 4 pages).*
Appleton (Am J. Pathol. 149(5); abstract only) 1996.*

* cited by examiner

*Primary Examiner* — Brandon Fetterolf
*Assistant Examiner* — Shirley V Gembeh
(74) *Attorney, Agent, or Firm* — Saliswanchik, Lloyd & Eisenschenk

(57) ABSTRACT

The present patent application relates to the use of triazine derivatives as cicatrising or angiogenic agents.

17 Claims, No Drawings

USE OF TRIAZINE DERIVATIVES FOR THE MANUFACTURE OF A MEDICAMENT HAVING A CICATRISING OR ANGIOGENIC EFFECT

FIELD OF THE INVENTION

The present invention relates in particular to the use of triazine derivatives or pharmaceutically acceptable salts thereof for the manufacture of a medicament having a cicatrising and/or angiogenic effect.

TECHNICAL BACKGROUND

The cicatrisation of wounds or related damage on different types of tissue generally depends on the proliferation of new epithelial, endothelial and connective tissue. It thus involves a series of co-ordinated cellular and molecular events. It may be retarded or modified by metabolic disruptions that accompany certain protracted diseases, such as venous insufficiency, arteritis, diabetes and even certain therapies.

Angiogenesis, the formation of new blood vessels from the pre-existing vascular network, is essential for the growth of any tissue. It takes place, inter alia, in damaged tissue during its cicatrisation. It is well known that disruption of angiogenesis is associated with the development of many diseases involving a deregulation of vascularisation. Many bibliographical data show, for example, a close link between the appearance of ulcers and the inhibition of angiogenesis in the case of diabetics. Furthermore, it is well documented that the endothelial cells constituting the blood vessels of the peripheral circulation are one of the many targets of damage induced by hyperglycaemia (diabetic microangiopathy). The pharmaceutical market currently offers many topical preparations recommended for the cicatrisation of wounds. In point of fact, their action results from the complementary nature of the various products of which they are composed and which gives them, to a certain extent, their cicatrising property. They protect wounds from the surrounding medium by means of an antiseptic dressing. They stimulate the development of vascularisation and regulate epidermisation. These topical forms consist mainly of a lipid mixture (lanolin, petroleum jelly, glycerol, etc.) to which are added acids (salicylic acid, benzoic acid or malic acid), minerals (zinc oxide or titanium oxide) or halides (starch iodide).

Certain preparations also contain collagen, fibrinogen, serum enzymatic proteolysate (supply of amino acids) or alternatively vitamins (vitamin A) or hormones (4-chlorotestosterone acetate).

A pomade also exists (Madecasol® tulgras from Laboratoires Syntex), the cicatrising action of which is provided by the addition of a mixture of three triterpenes extracted from roots of the plant *Centella asiatica* (TCEA).

These compounds exert their property by stimulating the biosynthesis of collagen and of glycosaminoglycans. However, these extracts may also give rise to contact allergies in patients.

It is known that one of the complications of diabetes lies in the appearance of skin complaints, such as ulcers (or even ulcerous necrotic angiodermatitis) or perforating dermatitis, which conventional medicaments used for the treatment of diabetes do not manage to control or treat.

DESCRIPTION OF THE INVENTION

The hypoglycaemiant properties of and preparations derived from triazines of the formula (I) have previously been described in FR 2 804 113 and WO 01/55122.

Unexpectedly, the applicant has now demonstrated that these compounds, or pharmaceutically acceptable salts thereof, also have a cicatrising and/or angiogenic effect.

More particularly, the invention relates to the use of derivatives of the general formula (I) below:

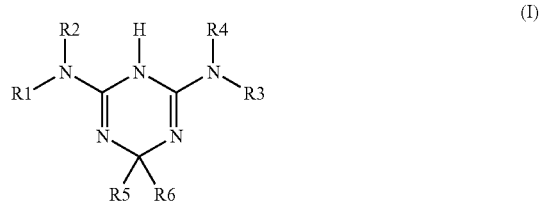

in which:
R1, R2, R3 and R4 are independently chosen from the following groups:
   H,
   (C1-C20)alkyl optionally substituted by halogen, (C1-C5)alkyl, (C1-C5)alkoxy or (C3-C8)cycloalkyl,
   (C2-C20)alkenyl optionally substituted by halogen, (C1-C5)alkyl or (C1-C5)alkoxy
   (C2-C20)alkynyl optionally substituted by halogen, (C1-C5)alkyl or (C1-C5)alkoxy
   (C3-C8)cycloalkyl optionally substituted by (C1-C5)alkyl or (C1-C5)alkoxy
   hetero(C3-C8)cycloalkyl bearing one or more heteroatoms chosen from N, O and S and optionally substituted by (C1-C5)alkyl or (C1-C5)alkoxy
   (C6-C14)aryl(C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
   (C6-C14)aryl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
   (C1-C13)heteroaryl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
R1 and R2, on the one hand, and R3 and R4, on the other hand, possibly forming with the nitrogen atom an n-membered ring (n between 3 and 8) optionally containing one or more heteroatoms chosen from N, O and S and possibly being substituted by one or more of the following groups: amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
R5 and R6 are independently chosen from the following groups:
   H,
   (C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
   (C2-C20)alkenyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C2-C20)alkynyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C3-C8)cycloalkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, hetero(C3-C8)cycloalkyl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C6-C14)aryl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C1-C13)heteroaryl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C6-C14)aryl(C1-C5)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 possibly forming with the carbon atom to which they are attached an m-membered ring (m between 3 and 8) optionally containing one or more heteroatoms chosen from N, O and S and possibly being substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, or possibly forming with the carbon atom a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl, (C1-C5)alkoxy, cyano, trifluoromethyl, carboxyl, carboxymethyl or carboxyethyl, R5 and R6 together also possibly representing the group =O or =S, the nitrogen atom of a heterocycloalkyl or heteroaryl group possibly being substituted by a (C1-C5)alkyl, (C3-C8)cycloalkyl, (C6-C14)aryl, (C6-C14)aryl(C1-C5)alkyl or (C1-C6)acyl group, and also the racemic forms, tautomers, enantiomers, diastereoisomers, epimers and mixtures thereof, and the pharmaceutically acceptable salts thereof, for the preparation of a medicament having a cicatrising and/or angiogenic effect.

The term "m-membered ring formed by R5 and R6" in particular means a saturated ring, such as a cyclohexyl, piperidyl or tetrahydropyranyl group.

The term "polycyclic group formed by R5 and R6" means an optionally substituted carbon-based polycyclic group and in particular a steroid residue.

One particular group of compounds of the formula (I) is that in which R5 is hydrogen.

Another particular group of compounds of the formula (I) is that in which R5 and R6 form with the carbon atom to which they are attached an m-membered ring (m between 3 and 8) optionally containing one or more heteroatoms chosen from N, O and S and possibly being substituted by one or more of the following groups: (C1-C5)alkyl, amino, hydroxyl, (C1-C5)alkylamino, alkoxy(C1-C5), (C1-C5)alkylthio, (C6-C14)aryl, (C6-C14)aryl(C1-C5)alkoxy, or form with the carbon atom a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl.

Another particular group of compounds of the formula (I) is that in which R5 and R6 are independently chosen from the following groups:

(C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl.

Preferably, R1, R2, R3 and R4 are independently chosen from H and (C1-C20)alkyl groups optionally substituted by halogen, (C1-C5)alkyl, (C1-C5)alkoxy or (C3-C8)cycloalkyl; more preferably, R1=R2=H and R3=R4=(C1-C20)alkyl optionally substituted by halogen, (C1-C5)alkyl, (C1-C5)alkoxy, (C3-C8)cycloalkyl or vice versa.

Preferably, R5 and R6 are independently chosen from H and (C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl; more preferably, R5=H and R6=(C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl or vice versa.

A more particular group of compounds of the formula (I) is that in which R1 and R2 are a methyl group and R3 and R4 represent a hydrogen.

Compounds of the formula (I) that may especially be mentioned include:

| | Formula | Salt |
|---|---|---|
| 1 | 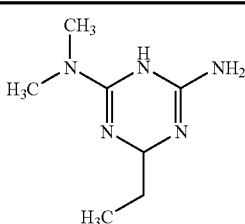 | HCl |

-continued
| | Formula | Salt |
|---|---|---|
| 2 | 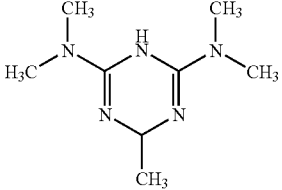 | HCl |
| 3 | 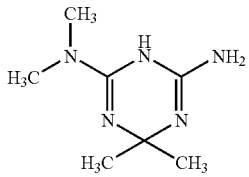 | |
| 4 | 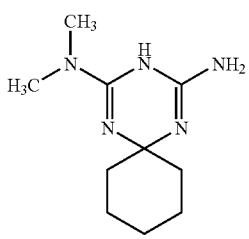 | HCl |
| 5 | 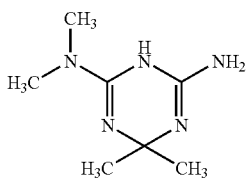 | Methane-sulfonate |
| 6 | 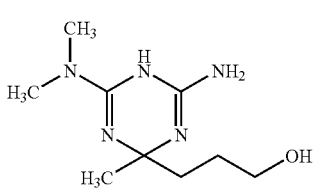 | |
| 7 | 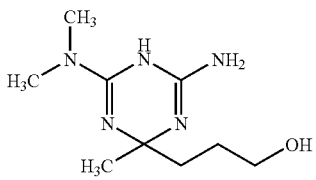 | HCl |
| 8 | 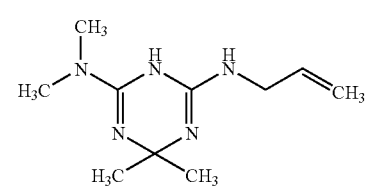 | HCl |
| 9 | 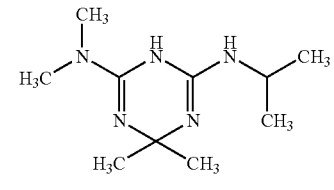 | HCl |

-continued

| | Formula | Salt |
|---|---|---|
| 10 | 6-phenyl-N2,N2-dimethyl-1,6-dihydro-1,3,5-triazine-2,4-diamine | HCl |
| 11 | 6-(4-methoxyphenyl)-N2,N2-dimethyl-1,6-dihydro-1,3,5-triazine-2,4-diamine | HCl |
| 12 | 6-(4-hydroxyphenyl)-N2,N2-dimethyl-1,6-dihydro-1,3,5-triazine-2,4-diamine | HCl |
| 13 | 6-(4-hydroxyphenyl)-N2,N2-dimethyl-1,6-dihydro-1,3,5-triazine-2,4-diamine | HCl |
| 14 | N2-ethyl-N4,N4,6,6-tetramethyl-1,6-dihydro-1,3,5-triazine-2,4-diamine | Fumarate |

-continued

| | Formula | Salt |
|---|---|---|
| 15 | (structure) | HCl |
| 16 | (structure) | HCl |
| 17 | (structure) | HCl |
| 18 | (structure) | HCl |
| 19 | (structure) | HCl |
| 20 | (structure) | Carbonate |
| 21 | (structure) | Carbonate |

-continued
| | Formula | Salt |
|---|---|---|
| 22 | 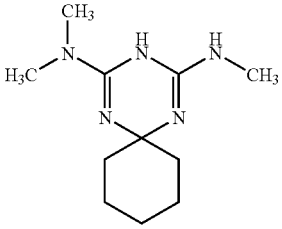 | HCl |
| 23 | 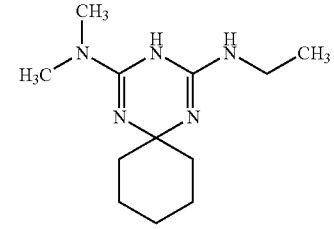 | HCl |
| 24 | 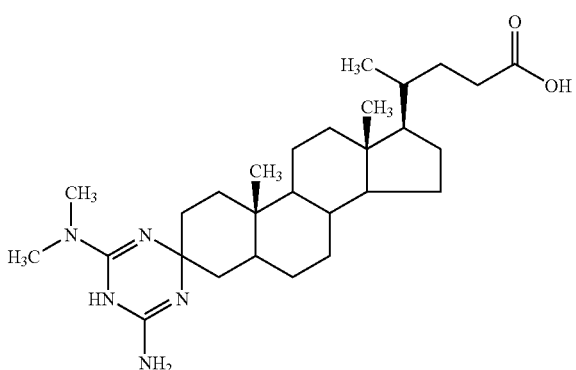 | HCl |
| 25 | 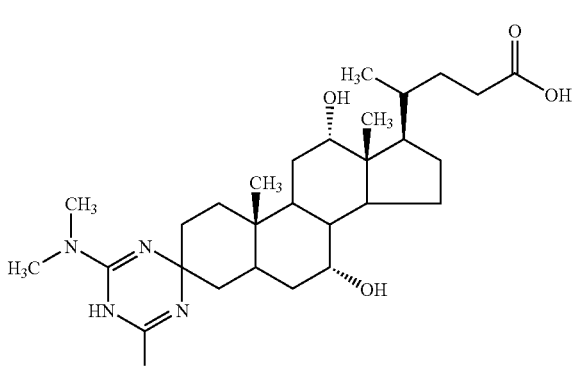 | HCl |
| 26 | 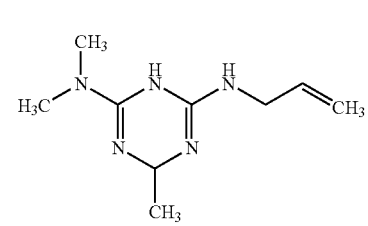 | HCl |

-continued

| | Formula | Salt |
|---|---|---|
| 27 | [structure: 2-amino-4-(dimethylamino)-1,3,5-triazine with spiro-cyclohexane bearing benzyloxy substituent] | HCl |
| 28 | [structure: 2-amino-4-(dimethylamino)-1,3,5-triazine with spiro-cyclohexane bearing OH substituent] | HCl |
| 29 | [structure: 2-amino-4-(dimethylamino)-1,3,5-triazine with 6-methyl-6-ethyl substitution] | Carbonate |
| 30 | [structure: 2-amino-4-(dimethylamino)-1,3,5-triazine with 6,6-diethyl substitution] | Carbonate |
| 31 | [structure: 2-amino-4-(dimethylamino)-1,3,5-triazine with spiro-cyclopentane] | HCl |
| 32 | [structure: 2-amino-4-(dimethylamino)-1,3,5-triazine with 6-propyl substitution] | Carbonate |

-continued

| | Formula | Salt |
|---|---|---|
| 33 | | HCl |
| 34 | | para-Toluene-sulfonate |
| 35 | | HCl |
| 36 | | para-Toluene-sulfonate |
| 37 | | para-Toluene-sulfonate |
| 38 | | HCl |

-continued

| | Formula | Salt |
|---|---|---|
| 39 | | HCl |
| 40 | | HCl |
| 41 | | para-Toluene-sulfonate |
| 42 | | HCl |
| 43 | | HCl |
| 44 | | HCl |

| Formula | Salt |
|---|---|
| 45 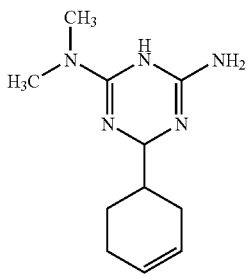 | para-Toluene-sulfonate | and more preferably the compound of Example 18.

According to yet another preferred embodiment, the invention relates more particularly to the use of compounds chosen from:
2-amino-3,6-dihydro-4-dimethylamino-6-methyl-1,3,5-triazine hydrochloride
(+)-2-amino-3,6-dihydro-4-dimethylamino-6-methyl-1,3,5-triazine hydrochloride
(−)-2-amino-3,6-dihydro-4-dimethylamino-6-methyl-1,3,5-triazine hydrochloride.

The compounds of the invention of the formula (I) as defined above, containing a sufficiently basic function, or both, may include the corresponding pharmaceutically acceptable salts of organic or mineral acids.

For the purposes of the present invention, the term "corresponding is pharmaceutically acceptable salts of organic or mineral acids" means any salt prepared from any non-toxic pharmaceutically acceptable organic or inorganic acid. Such acids include acetic acid, benzenesulfonic acid, benzoic acid, citric acid, carbonic acid, ethanesulfonic acid, fumaric acid, gluconic acid, glutamic acid, hydrobromic acid, hydrochloric acid, lactic acid, mandelic acid, malic acid, maleic acid, methanesulfonic acid, mucic acid, nitric acid, pamoic acid, pantothenic acid, phosphoric acid, succinic acid, tartaric acid and para-toluenesulfonic acid. Hydrochloric acid is advantageously used.

The invention also relates to the chiral salts of the compounds of the formula (I) used for the separation of the racemates.

By way of example, the following chiral acids are used: (+)-D-di-O-benzoyltartaric acid, (−)-L-di-O-benzoyltartaric acid, (−)-L-di-O,O'-p-toluoyl-L-tartaric acid, (+)-D-di-O,O'-p-toluoyl-L-tartaric acid, (R)-(+)-malic acid, (S)-(−)-malic acid, (+)-camphanic acid, (−)-camphanic acid, R-(−)-1,1'-binaphthalen-2,2'-diylhydrogenophosphonic acid, (+)-camphoric acid, (−)-camphoric acid, (S)-(+)-2-phenylpropionic acid, (R)-(+)-2-phenylpropionic acid, D-(−)-mandelic acid, L-(+)-mandelic acid, D-tartaric acid, L-tartaric acid, or a mixture of two or more thereof.

It will be appreciated that the compounds that are useful according to the present invention may contain asymmetric centres. These asymmetric centres may be, independently, in R or S configuration. It will be clear to a person skilled in the art that certain compounds that are useful according to the invention may also exhibit geometrical isomerism. It should be understood that the present invention includes individual geometrical isomers and stereoisomers and mixtures thereof, including racemic mixtures, of compounds of the formula (I) above. Isomers of this type can be separated from mixtures thereof by application or adaptation of known processes, for example chromatography techniques or recrystallisation techniques, or they are prepared separately from suitable isomers of their intermediates.

For the purposes of this text, it is understood that the tautomeric forms are included in the mention of a given group, for example thio/mercapto or oxo/hydroxy.

The enantiomers of the compounds according to the invention and the process for separating them are especially described in patent application WO 2004/089917, the content of which is incorporated herein by reference.

The present patent application also concerns the polymorphic forms of the compounds, as obtained according to patent application WO 2004/089917, for instance the A1 polymorphic form of the salt (+)-2-amino-3,6-dihydro-4-dimethylamino-6-methyl-1,3,5-triazine hydrochloride.

The present invention also relates to the other polymorphic forms of the compounds, such as the H1 polymorphic form of the salt (+)-2-amino-3,6-dihydro-4-dimethylamino-6-methyl-1,3,5-triazine hydrochloride, which can be prepared as follows:

Approximately 3 g of the A1 form of Example 18 are dissolved in 50 ml of 1 mol/l HCl at room temperature. The clear solution obtained is left to evaporate at room temperature, in an open beaker, until a solid residue crystallises.

The characterisation is performed by:
FT-IR Spectroscopy:
Brüker Vector 22
2 cm$^{-1}$ spectral resolution
32 scans
KBR discs (analogous to method A AA21505)
To evaluate the intensity of the IR bands, the IR spectra were normalised by vectorisation in the spectral range 4000-400 cm$^{-1}$ as an absorption spectrum.
Preadjustment was performed:
s: A>0.05
m: 0.01<A<0.05
w: A<0.01.
FT-Raman Spectroscopy:
Brüker RFS-100
excitation: 1064 nm
spectral resolution: 1 cm$^{-1}$
1000 mW
1000 scans
focalised
aluminium crucible (analogous to method RA AA21505)
To evaluate the intensity of the Raman bands, Raman spectra were normalised by vectorisation in the spectral range 3600-200 cm$^{-1}$. Preadjustment was performed:
s: A>0.05
m: 0.01<A<0.05
w: A<0.01

Powder X-Ray Diffraction (XRD)
diffractometer D5000 (Brüker AXS)
radiation CuKα1 at 1.5406 Å (U=30 kV, A=40 mA)
Transmission mode
Detector in sensitive position
Primary monochromator
Angle range: 3-65° 2θ
Stage width: 0.05° 2θ
Measuring time/stage: 1.4 s
The XRD machine is set at 2θ±0.1°.
Results
A1 Form:
XRD:

| No. | d[Å] | 2θ | I/Io |
|---|---|---|---|
| 1 | 5.98 | 14.8 | 85 |
| 2 | 5.26 | 16.8 | 83 |
| 3 | 4.35 | 20.4 | 30 |
| 4 | 3.57 | 24.9 | 100 |
| 5 | 3.50 | 25.4 | 53 |
| 6 | 3.36 | 26.5 | 96 |
| 7 | 3.31 | 26.9 | 52 |
| 8 | 3.04 | 29.3 | 57 |
| 9 | 2.90 | 30.8 | 30 |
| 10 | 2.74 | 32.7 | 35 |

FT-IR Bands (in cm$^{-1}$):
3384+/−1.5 (m), 3199+/−1.5 (m), 3163+/−1.5 (m), 3107+/−1.5 (m), 2993+/−1.5 (m), 2983+/−1.5 (m), 1652+/−1.5 (s), 1606+/−1.5 (s), 1576+/−1.5 (s), 1557+/−1.5 (s), 1505+/−1.5 (s), 1449+/−1.5 (m), 1427+/−1.5 (m), 1405+/−1.5 (m), 1383+/−1.5 (m), 1348+/−1.5 (m), 1306+/−1.5 (m), 1263+/−1.5 (w), 1235+/−1.5 (w), 1185+/−1.5 (w), 1096+/−1.5 (w), 1068+/−1.5 (w), 980+/−1.5 (w), 946+/−1.5 (w), 868+/−1.5 (w), 761+/−1.5 (w), 687+/−1.5 (m), 655+/−1.5 (m), 558+/−1.5 (w), 521+/−1.5 (w), 478+/−1.5 (w)

FT-Raman Bands (in cm$^{-1}$):
3217+/−1.5 (w), 2994+/−1.5 (m), 2983+/−1.5 (m), 2936+/−1.5 (s), 2883+/−1.5 (m), 1645+/−1.5 (w), 1602+/−1.5 (m), 1554+/−1.5 (m), 1453+/−1.5 (m), 1428+/−1.5 (m), 1349+/−1.5 (w), 1308+/−1.5 (w), 979+/−1.5 (m), 866+/−1.5 (w), 761+/−1.5 (w), 686+/−1.5 (s), 583+/−1.5 (m), 555+/−1.5 (s), 525+/−1.5 (m), 479+/−1.5 (m), 410+/−1.5 (m), 401+/−1.5 (m), 307+/−1.5 (m)

H1 Form
XRD:

| No. | d[Å] | 2θ | I/Io |
|---|---|---|---|
| 1 | 8.03 | 11.0 | 69 |
| 2 | 7.27 | 12.2 | 25 |
| 3 | 6.11 | 14.5 | 24 |
| 4 | 4.01 | 22.1 | 86 |
| 5 | 3.64 | 24.5 | 100 |
| 6 | 3.26 | 27.3 | 51 |
| 7 | 3.08 | 29.0 | 29 |
| 8 | 3.04 | 29.4 | 34 |
| 9 | 2.82 | 31.7 | 61 |
| 10 | 2.66 | 33.6 | 26 |

FT-IR Bands (in cm$^{-1}$):
3386+/−1.5 (m), 3080+/−3 (m), 1706+/−1.5 (s), 1691+/−1.5 (s), 1634+/−1.5 (m), 1513+/−1.5 (m), 1445+/−1.5 (w), 1241+/−1.5 (w), 1079+/−1.5 (w), 989+/−1.5 (w), 940+/−1.5 (w), 861+/−1.5 (w), 823+/−1.5 (w), 675+/−1.5 (w), 603+/−1.5 (w), 573+/−1.5 (w), 549+/−1.5 (w), 527+/−1.5 (w)

The compounds of the formula (I) above also include the prodrugs of these compounds.

The term "prodrugs" means compounds which, when administered to the patient, are chemically and/or biologically converted in the live body into compounds of the formula (I).

In the present description, the terms used have, unless otherwise indicated, the following meanings:

the term "(C1-C20)alkyl" denotes a linear or branched alkyl radical containing from 1 to 20 carbon atoms. Among the C1-C20 alkyl radicals that may especially be mentioned, in a non-limiting manner, are methyl, ethyl, propyl, isopropyl, butyl, sec-butyl, tert-butyl, pentyl, hexyl, octyl, decyl, dodecyl, hexadecyl and octadecyl radicals;

the term "(C1-C20)alkenyl" denotes a linear or branched hydrocarbon-based radical containing one or more unsaturations in double bond form. As alkylene radicals containing from 1 to 20 carbon atoms, mention may be made, in a non-limiting manner, of ethenyl, prop-2-enyl, but-2-enyl, but-3-enyl, pent-2-ynyl, pent-3-enyl and pent-4-enyl radicals;

the term "(C1-C20)alkynyl" denotes a linear or branched hydrocarbon-based radical containing one or more unsaturations in triple bond form. As alkylene radicals containing from 1 to 20 carbon atoms, mention may be made, in a non-limiting manner, of ethynyl, prop-2-ynyl, but-2-ynyl, but-3-ynyl, pent-2-ynyl, pent-3-ynyl and pent-4-ynyl radicals;

the term "alkoxy" refers to the term "alkyl-oxy";

the term "halogen" refers, in a non-limiting manner, to fluorine, chlorine or bromine;

the term "(C6-C14)aryl" refers to an aromatic group containing from 6 to 14 carbon atoms with at least one of the rings having a system of conjugated pi electrons, and including biaryls, which may be optionally substituted. Mention will be made in particular of biphenyl, phenyl, naphthyl, anthryl and phenanthryl radicals;

the term "hetero(C6-C14)aryl" refers to a 6-14-membered aromatic heterocycle containing 1-4 heteroatoms, the other atoms being carbon atoms. Among the heteroatoms, mention will be made in particular of oxygen, sulfur and nitrogen. Among the heteroaryl radicals, mention will be made more particularly of furyl, thienyl, pyridyl, pyrrolyl, pyrimidyl, pyrazinyl, oxazolyl, oxadiazolyl, isoxazolyl, quinolyl and thiazolyl radicals;

the term "(C3-C8)cycloalkyl" refers to a saturated hydrocarbon-based ring and contains monocyclic, bicyclic and polycyclic radicals containing from 3 to 8 carbon atoms. Mention will be made, in a non-limiting manner, of cyclopropyl and cyclobutyl radicals;

the term "(C6-C14)aryl(C1-C20)alkyl" refers to the corresponding -alkylaryl groups. Mention will be made in particular of benzyl and phenethyl groups.

The medicaments according to the invention may be in a form for local use, advantageously of the oil, cream, mousse, liniment, lotion, pomade, liquid, gel, milk, powder or spray type.

The forms may comprise a one-phase vehicle, consisting of a neutral hydroxypropylcellulose gel or of a charged gel formed from sodium carboxymethylcellulose. Creams, forms with a two-phase vehicle, comprising a hydrophilic phase dispersed in a lipophilic phase, can also be prepared.

Advantageously, the medicament contains from 0.02% to 2% by weight of the triazine derivative of the general formula (I) or of a pharmaceutically acceptable salt thereof and a suitable excipient. These excipients can be chosen from compounds that show good compatibility with these active principles. They are, for example, water-soluble polymers of natural polymer type, such as polysaccharides (xanthan gum, locust bean gum, pectin, etc.) or polypeptides, cellulose derivatives, such as methylcellulose, hydroxypropylcellulose or hydroxypropylmethylcellulose, or alternatively synthetic polymers, poloxamers, carbomers, PVA or PVP.

Finally, it is within the capacity of any person skilled in the art to add to these medicaments various excipients of co-solvent type, for instance ethanol, glycerol, benzyl alcohol, humectants (glycerol), diffusion aids (Transcutol, urea), or antibacterial preserving agents (methyl, butyl or propyl p-hydroxybenzoate at 0.15%, taken alone or as mutual combination).

In one particular embodiment of the invention, the triazine derivatives or pharmaceutically acceptable salts thereof are combined with at least one other active principle. This active principle may be, for example, of the type, such as an antibacterial, antifungal or antiviral agent, making it possible to accelerate the cicatrisation of damage and infected tissue, simultaneously or in combination with the treatment of the underlying infection.

This active principle may also consist of another agent for improving cicatrisation, such as epithelial growth factor, fibroblast growth factor, platelet-derived growth factor, etc.

The present invention also relates to a cicatrising pharmaceutical composition and/or a pharmaceutical composition having an angiogenic effect, for topical use, comprising, as active principle, a therapeutically effective amount of triazine derivatives of the general formula (I) or of pharmaceutically acceptable salts thereof, advantageously (+)-2-amino-3,6-dihydro-4-dimethylamino-6-methyl-1,3,5-triazine hydrochloride, in a suitable vehicle. The vehicle may be an excipient as described above. Advantageously, the composition contains from 0.02% to 2% by weight of the triazine derivative or of the pharmaceutically acceptable salt thereof.

Advantageously, the composition according to the present invention is in a pharmaceutical form for local use, advantageously of the type, such as a pomade, liquid, gel, milk, powder, spray, oil, cream, mousse, liniment or lotion.

In one preferred embodiment, the composition according to the invention contains at least one other active principle, as discussed previously.

The triazine derivatives of the general formula (I) and the pharmaceutically acceptable salts thereof, in particular (+)-2-amino-3,6-dihydro-4-dimethylamino-6-methyl-1,3,5-triazine hydrochloride, thus improve the cicatrisation of wounds or lesions of any type, including surgical incisions, thermal or chemical burns or burns caused by irradiation, abrasions, lacerations, amputations, ischaemic or decubitus ulcers, lesions or ulcers of the mouth, stomach or intestine or corneal lesions, and in particular those caused by a surgical operation performed on weakened or elderly individuals, treated by radiotherapy or chemotherapy, or diabetics. This is likewise the case for all dermatoses observed in the case of patients whose cutaneous circulation is deficient (erythemal lesions or vascularites) and all wounds observed in the case of diabetics. The pharmaceutical compositions and medicaments according to the invention appear to be beneficial even for the treatment of post-thrombotic tissue necroses, for example.

The frequency of application of the pharmaceutical formulation can vary within wide ranges (one to several times a day) as a function of the nature and severity of the wound, and also the age and weight of the individual.

The examples below of compositions according to the invention are given as non-limiting illustrations.

EXAMPLES

The amounts are expressed on a weight basis.

Formulation Example 1

Unit Formula for 100 grams of Gel (+)-2-Amino-3,6-dihydro-4-dimethylamino-6-methyl-1,3,5-triazine hydrochloride: 2 grams NaOH pellets: 0.01 gram
Hydroxyethylcellulose (Natrosol 250 HX): 2 grams
Monopotassium phosphate: 0.65 gram
Purified water: qs 100 grams Formulation Example 2

Unit Formula for 150 grams of Emulsion (+)-2-Amino-3,6-dihydro-4-dimethylamino-6-methyl-1,3,5-triazine hydrochloride: 1 gram.
33% Hydrocerine pomade (H/L) (hydrophilic phase dispersed in a lipophilic phase). (Fatty excipient from Roc®, containing petroleum jelly, liquid paraffin, triglycerides, polyoxyethylene ethers and ceresin): 98.80 grams
Methyl p-hydroxybenzoate: 0.2 gram
Purified water: qs 150 grams
Biological Results On diabetic rats (STZ), the induction of injuries and their quantification are determined on the backs of predetermined groups of rats.

The animals are anaesthetised, using a matrix painted with a tattoo dye. An incision 1.5×1.5 cm deep, including the panniculus carnosus muscle, is made in the middle of the back. The injuries accompanied by size markers are analysed with a digital camera at the time of injury and every three days up to the point of closure of the incision. The salt (+)-2-amino-3,6-dihydro-4-dimethylamino-6-methyl-1,3,5-triazine hydrochloride is studied after topical application at various concentrations and after several days of treatment.

The invention claimed is:

1. A method for producing a cicatrising effect in a patient comprising topically administering to wound or lesion of a patient in need thereof an effective amount of a compound that is (+)-2-amino-3,6-dihydro-4-dimethylamino-6-methyl-1,3,5-triazine, a tautomer and/or a pharmaceutically acceptable salt thereof.

2. The method according to claim 1, wherein said compound is in the form of a hydrochloride salt.

3. The method according to claim 1, wherein said compound or a pharmaceutically acceptable salt thereof is combined with one or more other antibiotic, antifungal or antiviral active agents.

4. The method according to claim 1, wherein the patient is not diabetic.

5. A method for cicatrising a wound or lesion in a patient comprising administering to said wound or lesion of a patient in need thereof an effective amount of a compound that is (+)-2-amino-3,6-dihydro-4-dimethylamino-6-methyl-1,3,5-triazine or a tautomer and/or a pharmaceutically acceptable salt thereof.

6. The method according to claim 5, comprising topically administering said compound to a patient with post traumatic tissue necrosis, an erythemial lesion or vascularities.

7. The method according to claim 5, comprising administering said compound to a surgical incision, a thermal or chemical burn, a burn caused by irradiation, an abrasion, a laceration, an amputation, a ischemic or decubitus ulcer, a lesion or ulcer of the mouth, a stomach or intestine or corneal lesion, a surgical lesion on a weakened or elderly patient, a lesion on a patient that was treated by radiotherapy, chemotherapy, or a lesion on a diabetic patient.

8. The method according to claim 7, wherein said compound is administered topically to a surgical incision.

9. The method according to claim 7, wherein said compound is administered topically to a thermal burn, a chemical burn or a burn caused by irradiation.

10. The method according to claim 7, wherein said compound is administered topically to an abrasion or a laceration.

11. The method according to claim 7, wherein said compound is administered topically to an ischemic or decubitus ulcer.

12. The method according to claim 7, wherein said compound is administered topically to an amputation site.

13. The method according to claim 7, wherein said compound is administered topically to a lesion or ulcer of the mouth.

14. The method according to claim 7, wherein said compound is administered to a stomach or intestine lesion.

15. The method according to claim 7, wherein said compound is administered topically to a corneal lesion.

16. The method according to claim 7, wherein said compound is administered topically to a surgical lesion on a weakened or elderly patient or to a lesion on a patient that was treated by radiotherapy.

17. The method according to claim 7, wherein said compound is administered topically to a lesion on a diabetic patient.

* * * * *

UNITED STATES PATENT AND TRADEMARK OFFICE
CERTIFICATE OF CORRECTION

PATENT NO. : 8,217,040 B2  
APPLICATION NO. : 12/160515  
DATED : July 10, 2012  
INVENTOR(S) : Gerard Moinet and Daniel Cravo Page 1 of 1

It is certified that error appears in the above-identified patent and that said Letters Patent is hereby corrected as shown below:

Title Page,
Item (74) Attorney, Agent or Firm, "Saliswanchik, Lloyd & Eisenschenk" should read --Saliwanchik, Lloyd & Eisenschenk--.

Column 22,
Line 21, "pent-2-ynyl" should read --pent-2-enyl--.

Signed and Sealed this
Fifth Day of February, 2013

Teresa Stanek Rea
*Acting Director of the United States Patent and Trademark Office*